United States Patent [19]

Matthews et al.

[11] Patent Number: 4,924,867
[45] Date of Patent: May 15, 1990

[54] TONOMETER APPARATUS

[75] Inventors: James R. A. Matthews, Old Windsor; Mervyn A. Little, Cambereley; John Fisher, Royston, all of Great Britain

[73] Assignee: Keeler Limited, Windsor, United Kingdom

[21] Appl. No.: 225,718

[22] PCT Filed: Nov. 4, 1987

[86] PCT No.: PCT/GB87/00777
§ 371 Date: Jul. 23, 1988
§ 102(e) Date: Jul. 23, 1988

[87] PCT Pub. No.: WO88/03384
PCT Pub. Date: May 19, 1988

[30] Foreign Application Priority Data

Nov. 7, 1986 [GB] United Kingdom ............... 8626601

[51] Int. Cl.⁵ .............................................. A61B 3/16
[52] U.S. Cl. .................................. 128/645; 128/646; 128/648; 128/652
[58] Field of Search ............... 128/645, 646, 648, 652, 128/748; 73/78; 351/211, 221

[56] References Cited

U.S. PATENT DOCUMENTS

| | | |
|---|---|---|
| 3,832,890 | 9/1974 | Grolman et al. ............... 128/648 |
| 4,386,611 | 6/1983 | Kantorski et al. ............. 128/645 |
| 4,724,843 | 2/1988 | Fisher ........................... 128/648 |

Primary Examiner—Randall L. Green
Assistant Examiner—Randy Shay
Attorney, Agent, or Firm—Lee, Mann, Smith, McWilliams & Sweeney

[57] ABSTRACT

A tonometer for measuring the intra-ocular pressure of an eye in which a pulse of fluid is projected towards the cornea of the eye to distort the corneal surface by the pressure of the pulse, the distortion in the corneal surface being detected by a change in the reflection of light directed onto the cornea. A constant volume chamber forms part of the fluid delivery system, with an inlet by which fluid under pressure can be supplied to the chamber when a fluid pulse is required. A lens assembly is fixed in the chamber wall for directing light toward an eye under test and a tube extends coaxially through the lens assembly to protrude internally into the chamber, where it is closed off at the end but includes a plurality of apertures in the internally protruding wall section to permit the controlled passage of fluid from the chamber into the tube.

6 Claims, 6 Drawing Sheets

TONOMETER APPARATUS

FIELD OF INVENTION

This invention relates to a tonometer of the non contact type for measuring the intra-ocular pressure of an eye.

BACKGROUND TO THE INVENTION

British Patent Specification No. 2175412 describes an improved from of non contact tonometer and methods of use.

It is an object of the present invention to provide an improved pneumatic feed for delvering pulses of air to an eye under test in such a tonometer.

It is a further object of the invention to provide an improved form of construction of the optical and pneumatic systems incorporated in the tonometer previously described.

SUMMARY OF THE INVENTION

According to the present invention there is provided a tonometer for measuring the intra-ocular pressure of an eye in which a pulse of fluid is projected towards the cornea of the eye to distort the corneal surface by the pressure of the pulse, the distortion in the corneal surface being detected by a change in the reflection of light directed onto the cornea characterised by:

(1) a constant volume chamber forming part of a fluid delivery system, (2) inlet means by which fluid under pressure can be supplied to the chamber when a fluid pulse is required, (3) lens means fixed in the chamber wall for directing light toward an eye under test, and (4) a tube which extends coaxially through the lens means and has a section which protrudes internally into the chamber where it is closed-off but includes a plurality of apertures in the interally protruding wall section to permit the controlled passage of fluid from the chamber into the tube.

The invention removes the criticality of the length of the tube protruding into the chamber (sometimes called the plenum chamber) and represents a distinct advantage over previously known arrangements in which it has proved necessary to adjust the length of the tube protruding into the plenum chamber so as to obtain optimum reproducability as between one air pulse and another during successive tests.

Preferably the chamber forms part of a housing which includes a first section which extends between the lens at the one end and a viewing eyepiece at the other and may accommodate a source of illumination, and an optical focussing and reflecting system.

The housing may include a second section within which the source of illumination is located.

The housing may include a third section containing the fluid inlet means and the light detection means.

Preferably one part of the housing, comprising the said third section and a portion of the first section of the housing leading from the third section to the apertured lens, is separated from the remainder of the housing by means of a semi-reflecting mirror fitted so as to represent a fluid-tight seal between the said one part and the remainder of the housing.

Typically at least a part of the wall of the housing is comprised of a printed circuit board forming at least a light tight seal with the housing, and electrical components required to be located within the housing are mounted on regions of the printed circuit board which communicate directly with the interior thereof.

The apertured lens means conveniently comprises a pair of aligned centrally apertured plano-convex lenses and the tube extends through the aligned apertures in the lenses, and a mask which determines the light pattern which is to form the final image on the light detection means is formed on one of the plane surfaces of the lenses.

The mask preferably comprises two slit like windows symmetrically arranged relative to the central opening and bounded by an opaque surround.

The invention will now be described by way of example, with reference to the accompanying drawings in which.

DETAILED DESCRIPTION OF THE DRAWINGS

Figures 1, 2, 3:
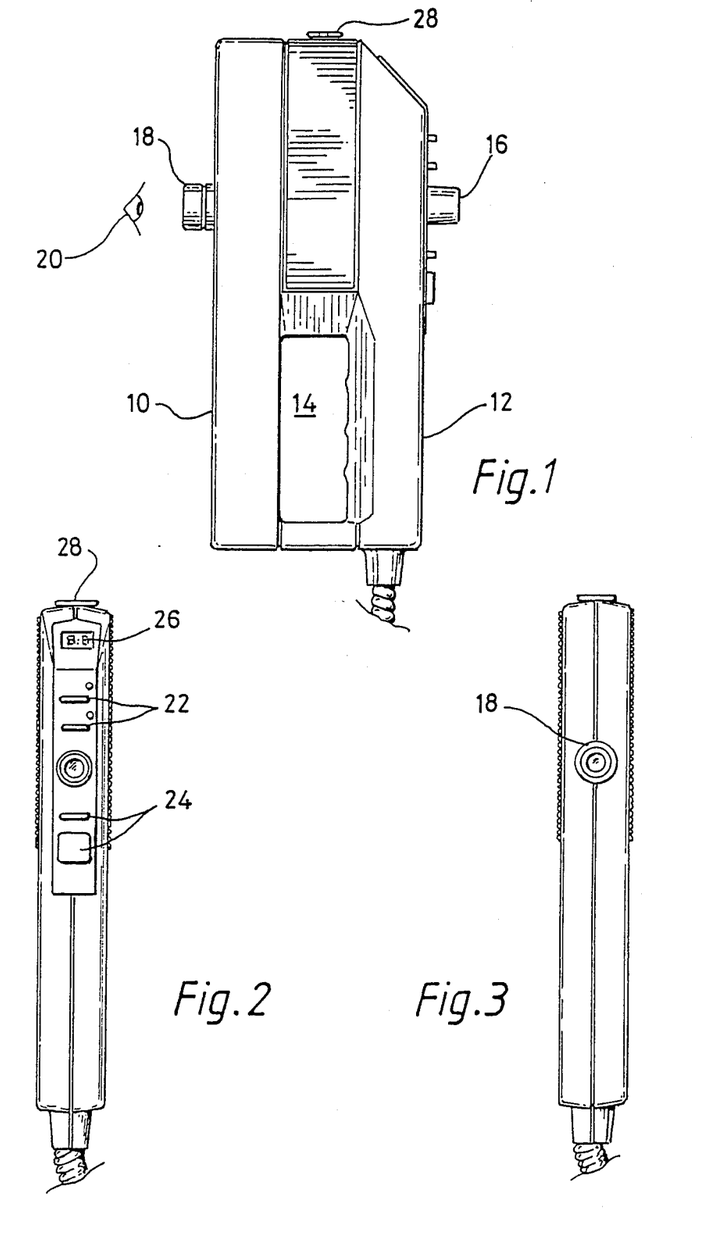
FIG. 1 is a side view of a hand held tonometer constructed in accordance with the invention.
FIG. 2 is a front view of the tonometer of FIG. 1.
FIG. 3 is a rear view of the tonometer shown in FIG. 1.

FIGS. 1, 2 and 3 show three views of a hand held tonometer embodying the invention. This comprises a casing generally designated 10 having a handgrip section 12 and a cut-out 14 through which the fingers of one hand can be inserted whilst grasping the handgrip section 12. The unit includes an eyepiece 16 and an inspection lens 18 which includes centrally an outlet for air pulses to be applied to an eye under test. The latter is shown diagrammatically at 20.

The user holds the instrument in the left or right hand and looks through the eyepiece 16 whilst positioning the unit all as described in our earlier application Ser. No. 8611901 to be published under Ser. No. 2175412.

On the rear of the unit are located various push-button switches such as 22 and 24 and a digital display device 26 for indicating a numerical value attributable to the intra occular pressure of the eye under test.

On the top of the unit can be seen the cap or cover 28 associated with the lamp housing to be described later.

Figure 4:
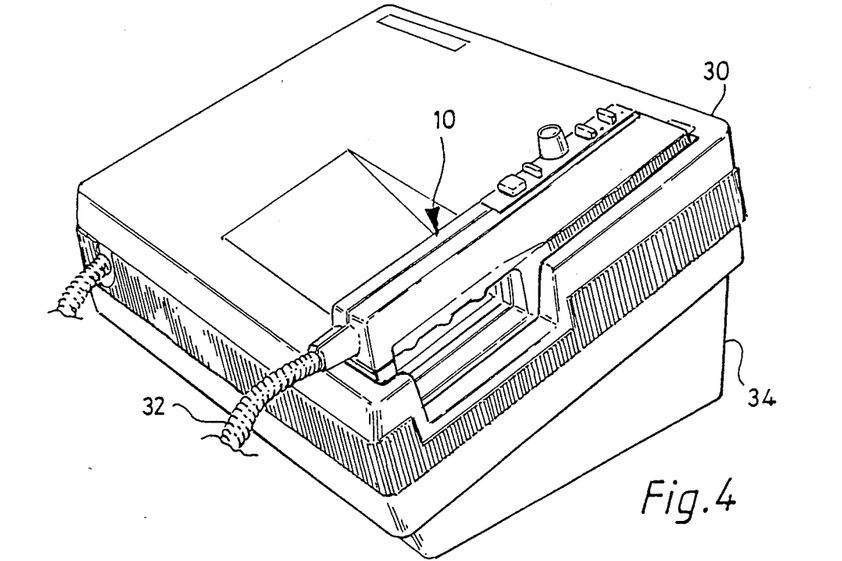
FIG. 4 is a perspective view showing the hand held tonometer installed in a base unit adapted to be placed on a horizontal surface such as a desk.

A base unit is provided into which the hand held unit can be fitted in use. The base unit includes a tilted upper section 30 which in the form shown in FIG. 4 provides that the handgrip section 12 is lower than the other end of the hand held unit when the latter is in position. The hand held unit is connected to the base unit via an umbilical cord 32 which houses an air line and electrical power cables as required.

Figure 5:
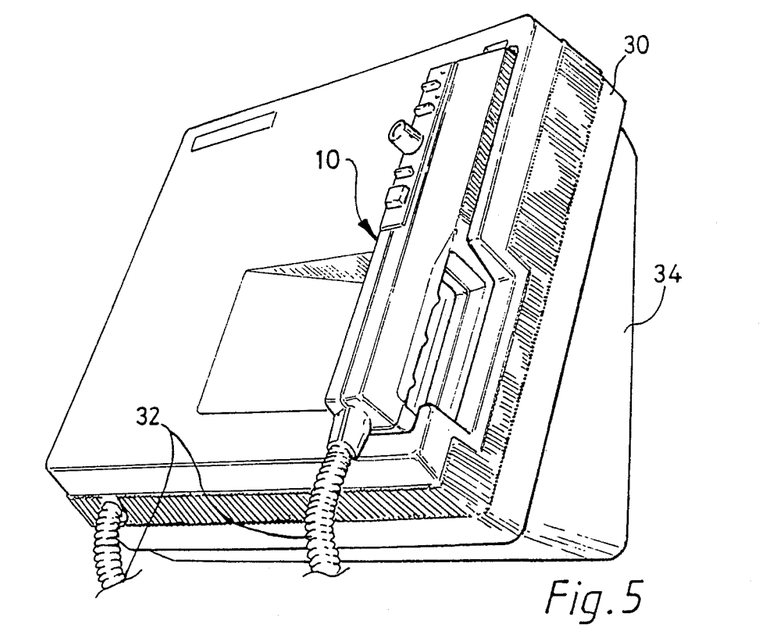
FIG. 5 is a perspective view of the hand held unit installed in a similar base unit but this time adapted for wall mounting.

In some situations it is preferable that the base unit be mounted on wall and to this end the lower part of the housing 34 can be removed from the upper part and rotated through 180° so that if then mounted on a vertical surface such as a wall, the upper part of the housing is now inclined in a manner so as to receive and support the unit 10 as shown in FIG. 5. In this mode the base unit can be thought of as a holster.

Figure 6:
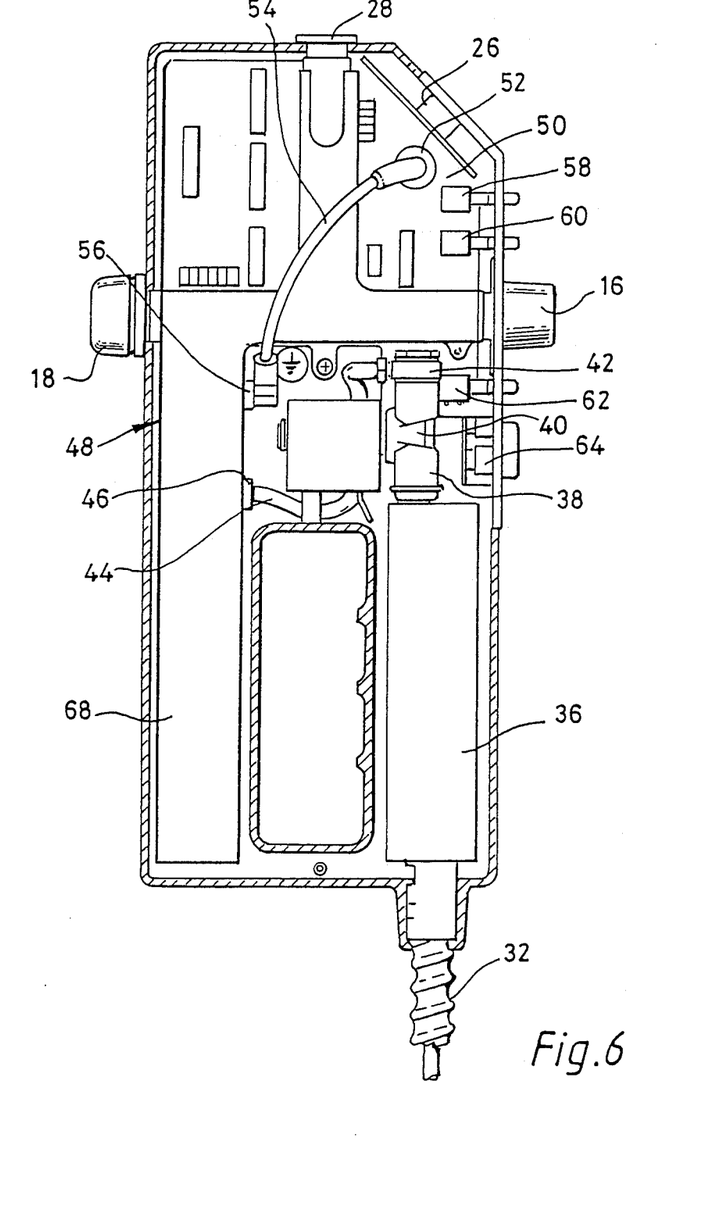
FIG. 6 is a side view of the unit shown in FIG. 1 with the nearside cover removed.

FIG. 6 illustrates the interior of the hand held unit which is revealed by the removal of the nearside casing of the unit 10 as shown in FIG. 1. Inside, the umbilical cord communicates with an air reservoir 36, an outlet of which is connected to the inlet of an air valve 38. The latter is solenoid operated, the solenoid being housed in housing 40 and the valve is normally closed. The outlet part of the valve 42 communicates via a tube 44 with an inlet 46 to a plenum chamber (not shown in FIG. 6) contained within the housing generally designated 48.

As will be described later, air from the plenum chamber escapes through a small orifice in the inspection lens 18. The pressure of the air in the plenum chamber is sensed by a pressure transducer located on a printed circuit board 50 and covered by a cylindrical housing 52 which itself communicates with the plenum chamber via a tube 54. The other end of the tube 54 is connected to an outlet 56 which extends through the wall of the plenum chamber in the housing 48.

Switches such as 58, 60, 62 and 64 are mounted on the printed circuit board 50 and have actuating buttons which protrude through the casing of the housing 10 as shown in FIGS. 1 and 2. Also visible in FIG. 6 is a two-digit digital display device 26 referred to in relation to FIG. 2.

The housing 48 includes a horizontal section which extends from the eyepiece 16 to the inspection lens 18, an upright limb designated 66 at the upper end of which is housed a lamp (to be described in more detail later) and a lower limb designated 68 which largely houses the plenum chamber—also to be described later.

Figures 7, 8:
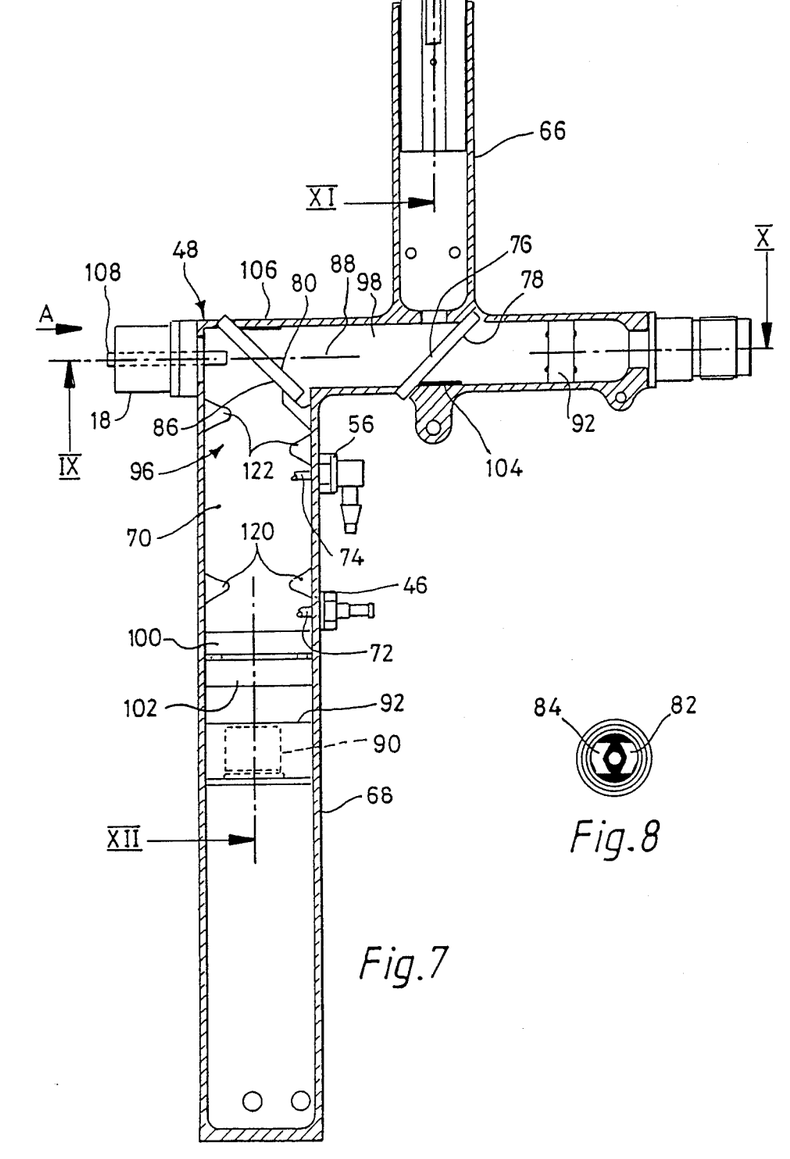
FIG. 7 is a side view of the housing containing the optical elements of the tonometer to an enlarged scale.
FIG. 8 is a view in the direction of the arrow A, and indicates the object pattern.

The housing 48 can be seen in more detail in FIG. 7 which is a cross-sectional view through the housing. In the region of the plenum chamber a coverplate 70 is fitted on the underside of the housing.

Thus the air inlet 46 is shown protruding into the plenum chamber at 72 and the air outlet for feeding the pressure transducer is shown with protruding pipe 74.

The housing contains a lamp which protrudes into the upper limb 66 and includes a cap or cover plate 28 by which the lamp can be withdrawn for replacement or cleaning. The lamp is typically held in position by means of a bayonett or screw thread as is also the cap 28.

Light from the lamp is reflected by the upper surface 76 of a first semi-reflecting mirror 78 located at an angle of 45° to the axis of the limb 66 and likewise at 45° to the axis of the central limb of the housing 48. Light is reflected towards and through a second semi-reflecting mirror 80 and illuminates an object which is located in the inspection lens assembly 18 and if viewed in the direction of arrow A will appear as shown in FIG. 8. Thus the only light which passes is that which is incident on the two shallow V shaped windows 82 and 84 and it is a pattern of those two windows which is formed on the eye and is reflected back through the inspection lens assembly 18. Some of the light incident on the lower surface 86 of the second semi-reflecting mirror 80 is reflected at right-angles to the axis 88 and after passing through a lens and transparent windows (to be described), is reflected by an inclined mirror 90 shown in dotted outline in FIG. 7, since it is located on an inclined face of a supporting plate 92 located within the housing limb 68.

Figure 12:
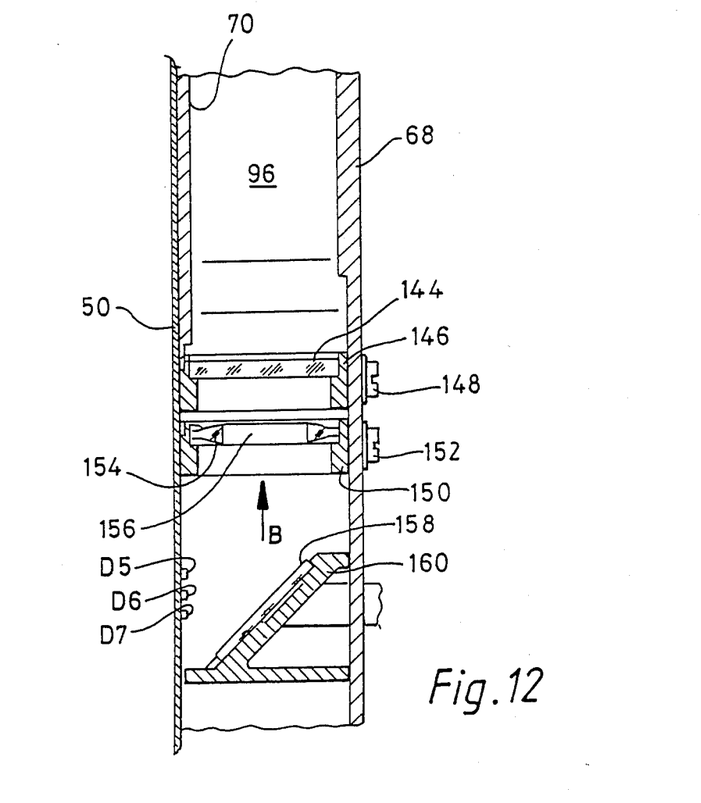
FIG. 12 is a cross-section through the lower limb of the housing shown in FIG. 7.

Light from the mirror 90 is reflected onto three photodiodes (shown in more detail in FIG. 12).

Light not reflected in this way by the lower surface 86 of the second semi-reflecting mirror 80, passes along the axis 88, through the semi-reflecting mirror 78 and after passing through a lens located in a lens mount 92 and a second lens mounted in the eyepiece 94, can be viewed by the observer.

The semi-reflecting mirror 80 may be cemented in position so as to completely close off the region 96 from the region 98 within the housing 48, but as will be described later, this is not the case in the embodiment as shown, and the air tight seal is instead provided around the optical element beyond the mirror 80 as will be described.

At the lower end of the plenum chamber 96 a glass plate 100 completely seals off the chamber the lower section of the limb 68 of the housing.

A constraint lens 102 is located below the glass plate 100.

In order to cut down on unwanted light reflectance, pads of black cotton velvet are located in the region of the semi-reflecting mirrors 78 and 80, at 104 and 106 respectively. The pad 104 absorbs any light which passes through the semi-reflecting mirror 80 and which if not absorbed might be reflected and would cause unwanted light in the optical system. Similarly the pad 106 is placed below the semi-reflecting mirror 80 to absorb any light passing through the latter after it has been reflected by the eye under test, together with any light reflected off the top surface at right angles to the main beam.

It is to be noted that the use of the two shallow V-shaped windows in the mask puts the light at the extremities of the apertures which introduces greater than usual problems with reflection from the surfaces of lenses and mirrors since the light is no longer concetrated along the optical axis as would normally obe the case in conventional optical systems.

Figure 9:
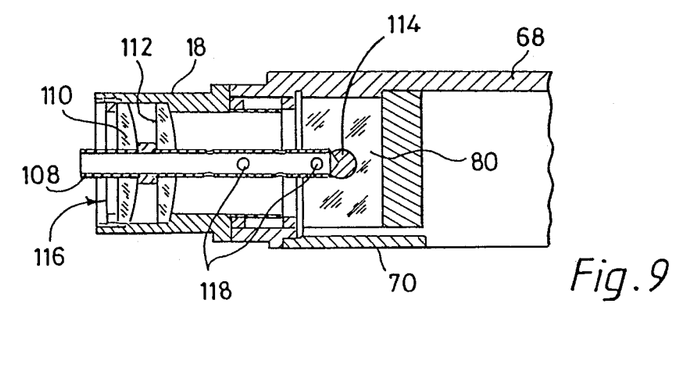
FIG. 9 is a cross-sectional view through the puff tube end of the housing of FIG. 7.

FIG. 9 is a cross-section on the optical axis of the housing 48 and shows the outlet from the plenum chamber (for feeding the pulses of air towards the eye under test) as comprising a tube 108 which protrudes centrally through two lenses 110 and 112 one of which has on its plane surface the mask shown in FIG. 8. In accordance with the invention, the tube protrudes rearwardly into the plenum chamber where its inward end is closed at 114. Air can pass from the chamber into the tube 108 via a series of apertures such as 118 which are formed in the wall of the tube beyond the second lens 112.

It is found in practice that by aperturing the wall of the tube in this way the length of the tube protruding into the plenum chamber is less critical than if an ordinary open-ended tube is used, where it is now well established that the inwardly protruding length must be accurately determined if optimum performance is to be obtained.

The provision of an apertured tube 108 thus has a distinct advantage over the use of a single open-ended tube since a further tight manufacturing tolerance has been removed from the assembly of the instrument.

Operation of the apertured tube 108 leading from the plenum chamber is believed to be as follows. The distributed mass and distributed elasticity of the air in the plenum chamber have time constants which are not negligibly short compared with the charging time of the plenum chamber. This arises from the fact that the plenum chamber is itself supplied through a relatively small bore tube. Thus oscillations and possibly turbulance arise within the plenum chamber so that at any instant there may be different pressures in different parts thereof. Whilst it may be possible by careful design of the chamber to select one particular point within the chamber at which the effects of oscillation and/or possibly turbulance are at a minimum, and to locate the entry to a single apertured puff tube at that point, the provision of a series of apertures produces an arrangement which is tolerant of manufacturing variations and does not require accurate adjustment to locate any one particular aperture at a point of minimal disturbance within the chamber as is characteristic of other designs.

Reverting to FIG. 7, the coverplate 70 is secured by means of screws or other fixings to two pairs of lugs shown at 120, 122, and this coverplate 70 can be seen in FIG. 9.

Referring back to FIG. 8, the mask defining the two V shaped windows 82 and 84 may be formed on the plane surface of the plano-convex lens 110 or 112. A protective glass window 116 fits over the open end of the tube 108 within which the lenses are housed and serves to protect the lens 110.

To the rear of the tube 108 is located the half silvered mirror or beam splitter 80 shown in FIG. 7, the half silvered mirror being cut and revealing its cross-section by virtue of the cross-sectional view.

As shown in FIG. 9, the mirror is secured along one edge to the inside of the closed wall of the housing 48 but there is a clearance between its opposite edge and the underside of the coverplate 70 fitted over the open face of the housing 48. This means that air can escape past the half silvered mirror 80 into the region 98 (see FIG. .) and to this end either the half silvered mirror 78 must be made a good air-tight fit across the housing or an air tight seal must be formed around the lens and lens mounting 92 to prevent the loss of air pressure at that end of the housing. Likewise, the lamp holder must be made a good air-tight fit within the limb 66.

Figure 10:
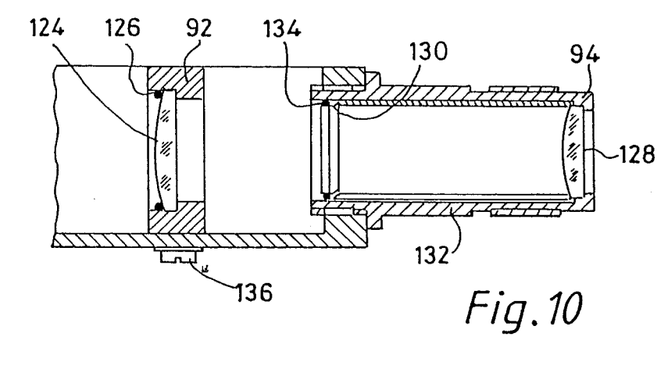
FIG. 10 is a cross-sectional view through the eyepiece end of the housing of FIG. 7.

FIG. 10 indicates in detail the construction of the lens mount 92 and the eyepiece generally designated 94. A plano-convex lens 124 is mounted within the lens mounting 92 and a seal 126 is provided around the periphery of the lens between it and the lens mount 92 to provide the air tight seal should this be required.

The eyepiece 94 is of fixed focal length and includes at its far end a second plano-convex lens 128. A window is formed af 130 at the inboard end of the tubular member 132 housing the lens 128, and a seal 134 is provided in the region of the window 130 to prevent the loss of air pressure should the seal 126 fail.

In addition to preventing the loss of air pressure, the air-tight seals provided within the instrument also prevent the ingress of dirt and moisture into the housing.

As shown in FIG. 10, the lens mount 92 is secured in position by means of one or more screws as at 136.

Figure 11:
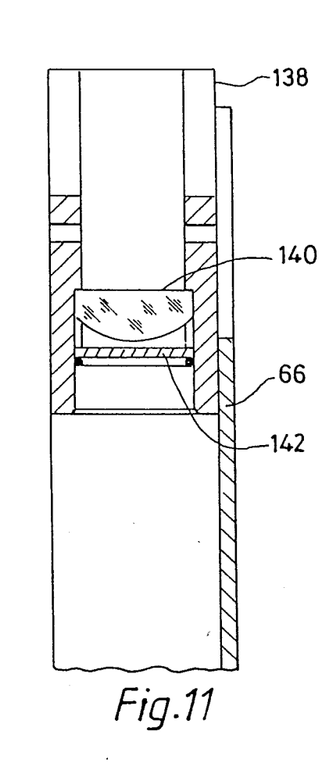
FIG. 11 is a cross-section through the lamp holder end of the housing of FIG. 7.

FIG. 11 gives detail of the lens associated with the lamp holder. The latter is in the form of a sleeve 138 which itself is an air-tight fit within the limb 66 of the housing 48. At the lower end of the sleeve 138 is a plano-convex lens 140 below which is located a transparent window 142 which is fitted with an air-tight seal within the interior of the tube 138. A lamp holder (not shown) can be slid into the sleeve 138 and located in position above the lens 140 and preferably a lens of very accurate dimensions with an accurately centred filament is employed so as to provide good uniform illumination from the condensing lens 140.

FIG. 12 shows in more detail the central region of the limb 68 of FIG. 7 which defines the lower extremity of the plenum chamber 96. The latter is closed off by means of a plate glass window 144 which is secured within a window frame 146, itself secured in position by one or more screws as at 148. Immediately therebelow is a lens mounting 150 secured in position by means again of one or more screws 152. A convex lens 154 is located within the lens mount 150. The central region of the lens has been removed as will be seen from FIG. 12 to leave a central circular aperture 156. A lens 61 is placed at a distance equal to its focal length from the plane of the photodiodes. Its function is to sharpen up the change in contrast with distance from the eye and to ensure that there is a major change in the contrast at the applanation event over the full working range of the instrument. Thus is achieved by providing an aperture in the central region of the lens through which light from a correctly aligned image will pass. However with mis-alignment or during the event when the image illumination is incident on the lens 61, the latter acts to focus the light down onto the central photodiode, decreasing the contrast.

Figure 13:
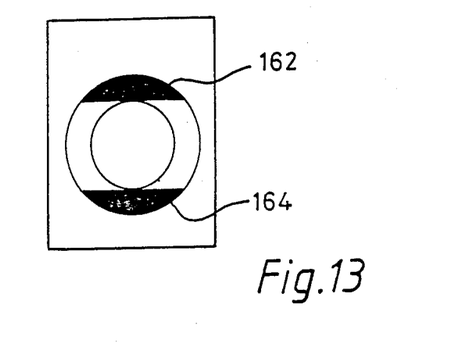
FIG. 13 is a view in the direction of arrow B in FIG. 12.

Formed on opposite regions of the lens or on the window are two marking strips as shown in FIG. 13 so that if viewed in the direction of arrow B in FIG. 12, the top and bottom regions of the lens are completely opaque.

Immediately below the lens is situated an inclined mirror 158 carried by a support 160. The latter extends across the interior of the housing limb 68 and supports the mirror 158 at 45° to the axis of the limb.

Whilst the plate 70 closes off limbs to define the plenum chamber, the face of the limb below the lens 154, is open thereby allowing three photodiodes D5, D6 and D7 mounted on a printed circuit board 50 to protrude into the interior of the limb to receive light directly from the mirror 158. The housing is positioned relative to the printed circuit board so that the diodes D5, D6 and D7 are at the correct point to receive the light from the mirror 158 so that when the instrument is correctly positioned relative to an eye under examination, the two outer diodes D5 and D7 receive light from the two V-shaped windows 82 and 84 of the mask at the front of the instrument, whilst the diode D6 receives no light at all.

The masking of the upper and lower regions of the lens 154 at 162 and 164 serves to cut out unwanted light and reduce reflections so as to more precisely obtain the differential illumination condition previously described with regard to photodiodes D5, D6 and D7.

We claim:

1. A tonometer for measuring the intra-ocular pressure of a eye in which a pulse of fluid is projected towards the cornea of the eye in use to distort the corneal surface by the pressure of the pulse, the distortion in the corneal surface being detected by change in the reflection of light directed onto the cornea characterised by:

(1) a source of light,
(2) a constant volume chamber forming part of a fluid delivery system,
(3) inlet means by which fluid under pressure can be supplied to the chamber when a fluid pulse is required,
(4) lens means fixed in a wall of the chamber for delivering light from the source to an eye under test,
(5) light detection means for receiving light reflected from the eye under test, and
(6) a tube which extends coaxially through the lens means and has a section which protrudes internally into the chamber where it is closed-off but includes a plurality of apertures in the internally protruding wall section to permit the controlled passage of fluid from the chamber into the tube.

2. A tonometer as claimed in claim 1 further comprising a viewing eyepiece wherein the chamber forms part of a housing which includes a first section which extends between the lens means at one end and said viewing eyepiece at an opposite end and accommodates a reflector which reflects light from the lens means into the eye piece.

3. A tonometer as claimed in claim 2 wherein the housing includes a second section within which a source of illumination is located.

4. A tonometer as claimed in claim 2 wherein the housing includes a third section containing the fluid inlet means and the light detection means.

5. A tonometer as claimed in claim 4 wherein the chamber is separated from the remainder of the housing by means of a semi-reflecting mirror forming a fluid-tight seal between the chamber and the remainder of the housing.

6. A tonometer as claimed in claim 1 wherein the apertured lens means comprises a pair of aligned centrally apertured plano-convex lenses and the tube extends through the aligned apertures in the lenses, and a mask which determines the light pattern which is to form the final image on the light detection means is formed on one of the plane surfaces of the lenses.

* * * * *